United States Patent
Ischdonat et al.

(10) Patent No.: US 7,323,085 B2
(45) Date of Patent: Jan. 29, 2008

(54) BASIS WEIGHT OF THE LINER IN A FIBROUS WEB

(75) Inventors: Thomas Ischdonat, Bachhagel (DE); Rudolf Muench, Koenigsbronn (DE)

(73) Assignee: Voith Paper Patent GmbH, Heidenheim (DE)

( * ) Notice: Subject to any disclaimer, the term of this patent is extended or adjusted under 35 U.S.C. 154(b) by 443 days.

(21) Appl. No.: 11/039,334

(22) Filed: Jan. 19, 2005

(65) Prior Publication Data
US 2005/0155735 A1  Jul. 21, 2005

(30) Foreign Application Priority Data
Jan. 20, 2004  (DE) .................... 10 2004 003 042

(51) Int. Cl.
*D21F 7/06* (2006.01)
*G01N 21/86* (2006.01)
*D21H 27/38* (2006.01)

(52) U.S. Cl. ................. 162/198; 162/125; 162/DIG. 6; 700/128; 356/429; 73/159

(58) Field of Classification Search ............... 162/199, 162/262, 263, 252–254, 298, 299, 123, 125, 162/126, DIG. 6, DIG. 10, DIG. 11; 250/339.1, 250/559.1; 73/159; 700/127–129; 356/429–431; 118/665
See application file for complete search history.

(56) References Cited

U.S. PATENT DOCUMENTS

| | | | |
|---|---|---|---|
| 3,207,901 A | 9/1965 | Barker, Jr. ................. 250/83.3 |
| 4,577,104 A | 3/1986 | Sturm ........................ 250/339 |
| 4,840,706 A | 6/1989 | Campbell ................... 162/198 |
| 4,957,770 A * | 9/1990 | Howarth ........................ 427/9 |
| 5,020,356 A * | 6/1991 | Dukes ........................... 73/865 |
| 5,455,422 A * | 10/1995 | Anderson et al. ........ 250/341.1 |
| 6,183,561 B1 * | 2/2001 | Belotserkovsky ........... 118/665 |
| 6,229,612 B1 | 5/2001 | Koo ............................. 356/433 |
| 6,495,831 B1 * | 12/2002 | Hyvarinen et al. .... 250/339.07 |
| 6,870,619 B1 | 3/2005 | Tenhunen et al. ........... 356/330 |
| 2003/0132387 A1 | 7/2003 | Tenhunen et al. ...... 250/339.11 |

FOREIGN PATENT DOCUMENTS

| | | |
|---|---|---|
| GB | 1 604 747 | 5/1978 |
| JP | 11-237377 | * 8/1999 |
| JP | 11237377 | 8/1999 |

* cited by examiner

*Primary Examiner*—Eric Hug
(74) *Attorney, Agent, or Firm*—Taylor & Aust, P.C.

(57) ABSTRACT

A method for determining the basis weight of a first ply of a fibrous web, which covers a second ply of the fibrous web including the steps of positioning an electromagnetic transmitter and an electromagnetic receiver, radiating the fibrous web, receiving a measuring signal and a reference signal, and determining the basis weight. The positioning an electromagnetic transmitter and an electromagnetic receiver step includes positioning them proximate to a side of the first ply. The radiating the fibrous web step is accomplished by the electromagnetic transmitter radiating the fibrous web with at least one measuring wavelength and at least one reference wavelength, the second ply having different optical characteristics at the measuring wavelength than at the reference wavelength. The receiver receives a measuring signal, which is returned at the measuring wavelength and the receiver receives a reference signal that is returned at the reference wavelength. The basis weight of the first ply being determined by utilizing a comparison of the measuring signal and the reference signal.

11 Claims, 4 Drawing Sheets

Fig. 1
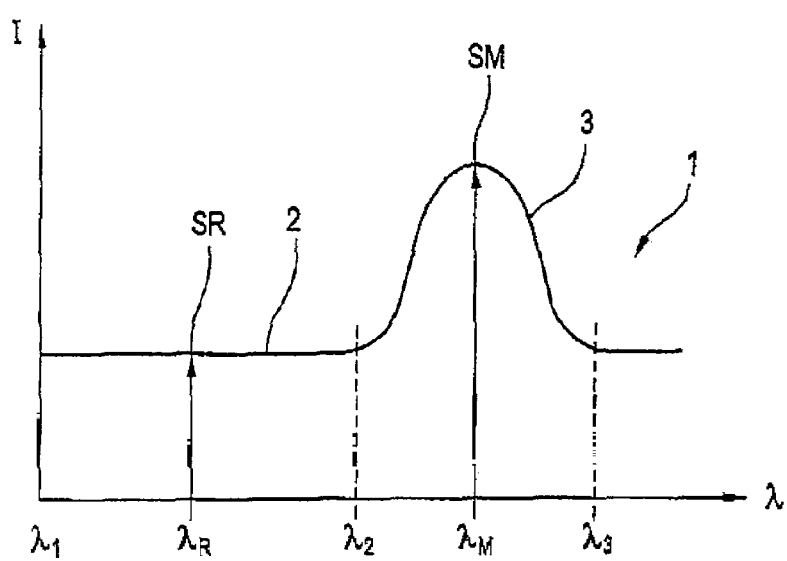
a)
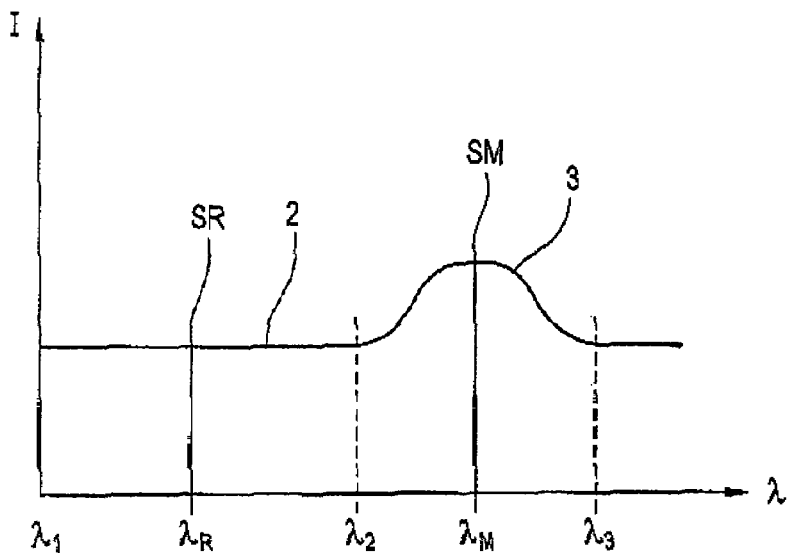
b)
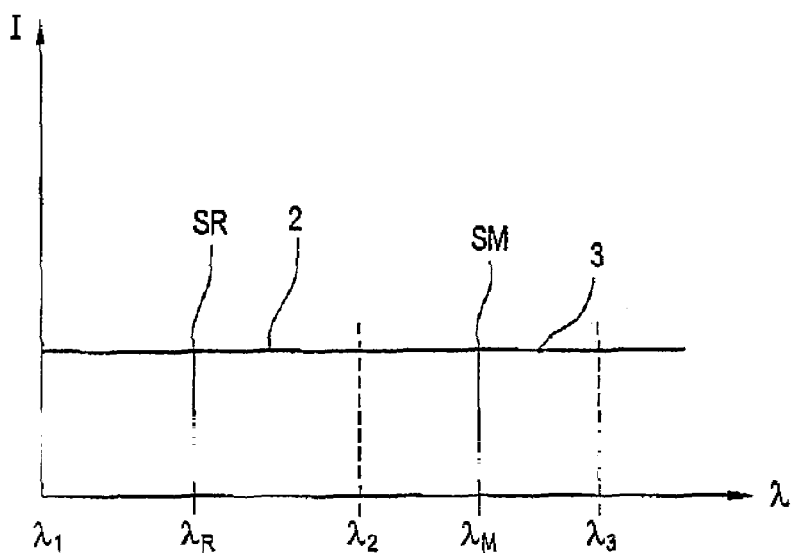
c)

BASIS WEIGHT OF THE LINER IN A FIBROUS WEB

BACKGROUND OF THE INVENTION

1. Field of the Invention

The present invention relates to a method to determine the basis weight of the top ply or liner in a fibrous web, as well as to a method to regulate the basis weight.

2. Description of the Related Art

Cardboard usually consists of a top and a bottom liner between which one or more intermediate plies are located. A liner is normally produced from bleached cellulose or from other high-grade fibers and is responsible for the appearance and the printability of the cardboard. The intermediate ply is normally produced from a low grade fiber stock.

Because a show-through of the intermediate ply considerably impairs the appearance and the printability of the cardboard, the liner must have a basis weight sufficient to prevent the intermediate ply from showing through. However, a liner basis weight which is too high contains too great a component of high-grade fibers, resulting in higher associated costs.

Various methods for the determination of liner basis weights have been previously suggested. Among them is a method that provides for the basis weight to be determined by way of taking a brightness measurement, in accordance with TAPPI T-452. With this method, the relative reflection from the liner is measured at 457 nm. With this method the reflection signal is strongly dependent upon brighteners and fillers in the liner. In spite of a high TAPPI brightness the liner may display insufficient opacity and may inadequately conceal the intermediate ply.

Another method is the determination of the CIE brightness of the liner. This method takes measurements over the entire visible spectrum. It is however, also dependent upon brighteners and fillers in the liner.

What is needed in the art is a more dependable, less expensive determination of the basis weight, whereby the basis weight is determined almost independently from the influence of brighteners or fillers.

SUMMARY OF THE INVENTION

If a second ply of a fibrous web, which is covered totally or partially (translucently), by a first ply, possesses different optical characteristics, over at least two different wavelengths, then a conclusion may be reached regarding the basis weight of the top first ply. The conclusion is based on radiation of the fibrous web with electromagnetic radiation and based on comparisons of the signals sent from the fibrous web over the two wavelengths. Such conclusions may be reached independently of the brightness of the illumination of the fibrous web, or independent of brighteners, etc. in the fibrous web.

The finding is based on the fact that, due to the different optical characteristics of the second ply, relative to the two wavelengths, the second ply contributes in varying degrees relative to the two wavelengths to the integral signals from the first and second ply of the fibrous web.

The current invention takes advantage of this finding and suggests a method whereby the basis weight of a first ply of a fibrous web, which covers a second ply of a fibrous web is determined through the following steps:

Provision of an electromagnetic transmitter and an electromagnetic receiver on the side of the first ply, Radiation of the fibrous web with the transmitter transmitting at least one measuring wavelength and at least one reference wavelength, whereby the second ply has different optical characteristics with the measuring wavelength than with the reference wavelength, The receiver picks up the measuring signal, which is received at the measuring wavelength, and the reference signal which is received at the reference wavelength, and Determination of the basis weight by utilizing a comparison of the measuring signal and the reference signal.

The fibrous web can be radiated at one or more discrete measuring wavelengths or reference wavelengths, as well as in a measuring wavelength range or reference wavelength range. In addition, the fibrous web may also be radiated in a wavelength range that includes one or more measuring wavelengths, or a measuring wavelength range and one or more reference wavelengths or a reference wavelength range.

In accordance with another embodiment of the present invention, the second ply displays a higher reflection capacity or a higher absorption capacity over the measuring wavelength than over the reference wavelength.

Intermediate plies of lined cardboard consist generally of low quality lignin-containing fiber stocks, whereas liners, as a rule, consist of high quality lignin-free fiber stocks. It is known from research that lignin-containing stocks display an especially high reflection capacity or absorption capacity at certain characteristic wavelengths.

In the event that a liner does not cover the intermediate ply of a fibrous web completely so that the intermediate ply shows through, then the measuring signal picked up by the receiver from the fibrous web will, with the characteristic wavelengths, contain an especially high signal component from the intermediate ply. In other words, the measuring signal contains a high reflection content or high absorption content of the intermediate ply, in addition to the components from the liner. With increasing coverage of the intermediate ply by the liner, the signal component of the liner dominates more and more in the characteristic wavelengths. With the characteristic wavelengths, the intermediate ply therefore provides a contribution to the measuring signal which is strongly dependent upon the basis weight of the liner. Subject to the basis weight of the liner, this contribution may or may not dominate the measuring signal.

With wavelengths that are outside the characteristic wavelengths, that is wavelengths where the intermediate ply has a lower reflection capacity/absorption capacity than with the characteristic wavelengths, the measuring signal, independent of the liner basis weight, is defined to a lesser degree by the intermediate ply than would be the case with the characteristic wavelengths. This means there is less of a dependency of the measuring signal upon the intermediate ply, than with the characteristic wavelengths.

With the wavelengths that are outside the characteristic wavelengths, the intermediate ply therefore provides a contribution to the measuring signal, which is essentially independent from the basis weight of the liner. This being independent of the liner basis weight, it does not dominate the measuring signal.

According to a method of the present invention a measuring signal is detected with a characteristic wavelength, whereby the signal contains a contribution that is heavily dependent on the basis weight of the liner. In order to determine the contribution of the intermediate ply the measuring signal is compared and, for example, standardized with a reference signal at a wavelength outside the characteristic wavelengths. The contribution is a measure for the basis weight of the liner independently from, for example, the degree of brightness of the liner which is subject to brighteners and/or fillers.

According to one embodiment of the present invention, the web is radiated in a measuring wavelength range and/or a reference wavelength range. This means that the fibrous web receives a spectrum of electromagnetic radiation, which extends from the beginning to the end of the measuring wavelength range and/or the reference wavelength range. It further means that the measuring signals received in the measuring wavelength range and the reference signals received in the reference wavelength range are picked up by the receiver and that the basis weight is subsequently determined by comparison of the measuring signals with the reference signals.

In this context, the measuring wavelength range refers to a wavelength range where the second ply of the fibrous web has other optical characteristics than in the wavelength range, which is referred to as the reference wavelength range.

In accordance with one embodiment of the present invention, the measuring wavelength range is between 550 and 620 nm, especially between 570 nm and 590 nm. Research has shown that lignin-containing stocks have a clearly increased reflection capacity in this wavelength range, as compared to other wavelength ranges.

Research has further shown that lignin-containing stocks possess aromatic structures and therefore absorption bands in the UV spectral region. The absorption bands are at 280 nm and 310 nm. Accordingly, one embodiment of the present invention provides that measuring wavelengths are in the range of 280 nm and/or in the range of 310 nm.

In addition, lignin-containing stocks possess absorption bands in the infra-red (IR) spectral region. IR-radiation penetrates further into liners having greater basis weights, than radiation of the UV—or visual spectral region. Accordingly, a preferred design variation of the invention provides that the measuring wavelength range is in the IR-spectral region.

Obviously, a combination of the aforementioned measuring wavelengths and measuring wavelength ranges are also possible.

According to an additional embodiment of the present invention, the reference wavelength range is in the visual blue spectral region.

Yet an additional embodiment of the inventive method provides that the basis weight (BW) is determined by using the formula BW=A*exp(-YI*B), whereby A and B represent equipment-specific constants and YI is the value that is determined by comparing the reference signal and the measuring signal. There are various possibilities to determine the value YI in order to calculate the basis weight. One possibility provides that the value YI is determined by the creation of a ratio between the reference signal and measuring signal. Most of the commonly used spectrophotometers are designed so that they determine the standard color values X, Y and Z from the measured reflection spectrums of the sample. Accordingly, it is advantageous if the determined standard color values are utilized for the calculation of the YI value.

Yet another embodiment of the present invention provides that the YI value is determined from the standard color values Y and Z by utilizing the formula YI≈(Y−Z)/Y (Yellowness-Index according to ADTM E-313 Standard). The YI value, in accordance with the ASTM E-313 Standard, is the so-called Yellowness-Index of the sample. The standard color value with a maximum in the blue spectral region is subtracted from the standard color value with maximum in the yellow-orange spectral region to determine the YI value.

The calculation of the YI value according to the ASTM E-313 Standard is meaningful in the analysis of the measuring wavelength range between 550 nm and 620 nm, especially between 570 nm and 590 nm. Tests have shown that a sufficient liner basis weight must be used, if the Yellowness Index is <1.

The measuring wavelength range of between 550 nm and 620 nm, especially between 570 nm and 590 nm is in the range of the maximum of the standard color value function X, whereas this wavelength range is outside the maximum of the standard color value function Y. To improve the signal to noise ratio it is useful if the YI value is determined from the standard color values X, Y and Z with the formula YI≈(Cx*X−Cy*Z)/Y, whereby Cx and Cy represent equipment-specific constants.

In order to accurately determine the basis weight it is certainly useful if status information of the web converting machinery and/or machinery parameters of the web converting machinery are utilized for the determination of the basis weight. One variation of the present invention provides that the basis weight is determined by utilizing status information and/or machinery parameters of web converting machinery. Status information may, for example, be the current headbox flow rate. A machinery parameter may, for example, be the adjusted machinery speed.

In addition, it is the intent of the present invention to suggest a method to regulate the basis weight of a fibrous web, which among other things, utilizes the previously described method for determination of the basis weight in order to regulate the basis weight.

The method for regulating the basis weight of a ply in a fibrous web provides that the basis weight is determined at several locations in machine direction (MD) and/or a cross direction (CD) by way of a method in accordance with one of claims 1 through 11, and that a control unit provides control signals to one or more actuators on the basis of the determined basis weight.

According to one embodiment of the present invention, one or more actuators are provided which control the dilution water of the headbox, adjustments of the slice bars and/or lips of the headbox, etc.

BRIEF DESCRIPTION OF THE DRAWINGS

The above-mentioned and other features and advantages of this invention, and the manner of attaining them, will become more apparent and the invention will be better understood by reference to the following description of embodiments of the invention taken in conjunction with the accompanying drawings, wherein:

FIG. 1 shows the relative intensity of the light which is reflected by the fibrous web subject to the wavelength, at various liner basis weights;

Corresponding reference characters indicate corresponding parts throughout the several views. The exemplifications set out herein illustrate one preferred embodiment of the invention, in one form, and such exemplifications are not to be construed as limiting the scope of the invention in any manner.

DETAILED DESCRIPTION OF THE INVENTION

Figure 2:
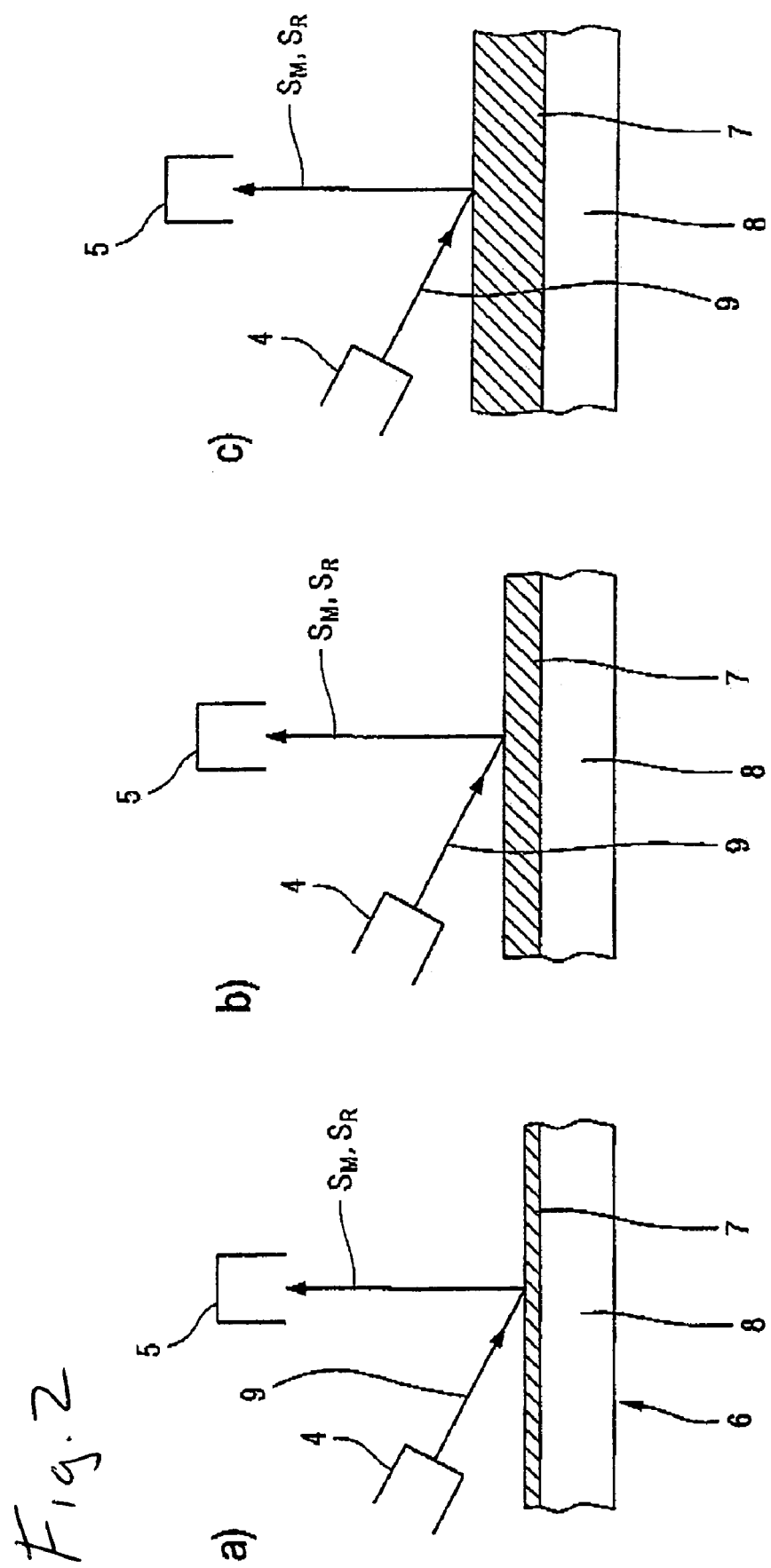
FIG. 2 is an arrangement of measuring devices of embodiments of the present invention.

Referring now to the drawings, and more particularly to FIG. 1 there is illustrated the intensity of the light reflected by a fibrous web 6 subject to the wavelength, at various basis weights of a liner 7 (also see FIG. 2).

Curve 1, illustrated in FIG. 1, represents the integral reflection signal from the overlay of the reflection signals of first liner 7 and second intermediate ply 8 of fibrous web 6. Curve 1 is obtained by an addition of the standard color values X, Y and Z and subsequent multiplication of the sum with the illumination function of transmitter 4, that is embodied as a light source. Curve 1 illustrates curve ranges 2 and 3.

Curve range 2 extends in wavelength range $\lambda_1$ to $\lambda_2$, as well as $\lambda$ greater than $\lambda_3$, progresses horizontally and displays the wavelength ranges with the same intensity. In the present example the reflection signals of the first and the second ply in curve range 2, create an essentially white or gray background.

Curve range 3 progresses in the wavelength range of $\lambda_2$ to $\lambda_3$ and subject to the basis weight of the first ply, shows a peak-type progression with an increased level or with the same intensity as the curve of range 2. Accordingly, the second ply in curve range 3 has a significantly increased degree of reflection, compared to curve range 2.

According to the present invention the measuring wavelength $\lambda_M$ is selected so that it is located in curve range 3. It is however also feasible to select a measuring wavelength range that extends from wavelength $\lambda_2$ to wavelength $\lambda_3$. In the present example, the measuring wavelength $\lambda_M$ is at a wavelength in the range of between 570 nm and 590 nm, or the measuring wavelength range is between 570 nm and 590 nm. In addition, and in accordance with an embodiment of the present invention, the reference wavelength $\lambda_R$ is selected so that this is within curve range 2. It is also feasible to select a reference wavelength range that would extend, for example, from wavelength $\lambda_1$ to the wavelength $\lambda_2$.

In FIG. 1a the first ply of the fibrous web has a low basis weight. This means that the second ply of the fibrous web is covered only slightly by the first ply. For this reason, FIG. 1 shows a measuring signal SM having a high intensity, as compared to reference signal SR.

In FIG. 1b the basis weight of the first ply is increased when compared to the basis weight in FIG. 1a. Accordingly, the signal contribution of the second ply to the total signal in the curve range is reduced. Accordingly, the intensity ratio between measuring signal SM and reference signal SR as compared to that of FIG. 1a is clearly reduced.

In FIG. 1c the basis weight of the first ply is increased to such an extent, that a dominant signal contribution by the second ply can no longer be observed in curve range 3. The reflection signal is composed in the same manner as the reflection signal in curve 2. Measuring signal SM and reference signal SR have the same intensity.

Now, additionally referring to FIG. 2, there is shown a side view of a measuring device arrangement for the implementation of the present method. As can be seen in FIG. 2, the arrangement includes a transmitter 4 and a receiver 5 for the purpose of transmitting and receiving light 9. Transmitter 4 transmits light 9 at least at a wavelength $\lambda_M$, or within a measuring wavelength range and at a reference wavelength $\lambda_R$ or within a reference wavelength range. In the present design example a measuring signal SM and a reference signal SR will be reflected or transmitted in both wavelengths by fibrous web 6.

Measuring signal SM and reflective signal SR each are composed from components that were reflected from liner 7 and from intermediate ply 8.

Here, measuring signal SM, subject to the basis weight of liner 7, possesses a clearly varied signal component from intermediate ply 8, which has a significantly higher reflection capacity at measuring wave length $\lambda_M$, or in the measuring wavelength range, compared to the reference wavelength $\lambda_R$ or the reference wavelength range.

FIGS. 2a through 2c illustrate different basis weights for liner 7, in correlation to the intensity spectrums in FIGS. 1a through 1c.

Figure 3:
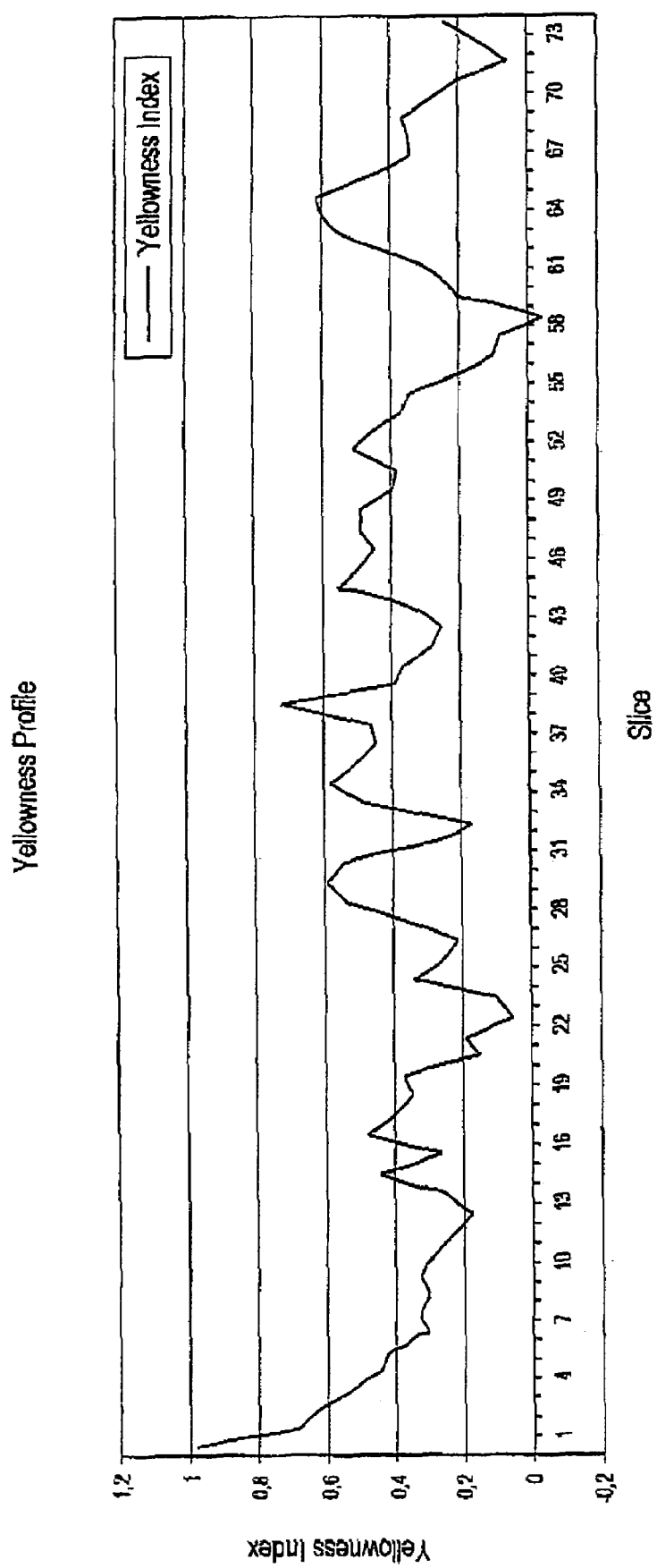
FIG. 3 illustrates the Yellowness Index in a cross profile of a fibrous web.

Now, additionally referring to FIG. 3, there is illustrated the Yellowness Index in a fibrous web, shown in a cross-directional profile, with a basis weight of the first ply or liner, which is sufficient to cover the second or intermediate ply. As can be seen by FIG. 3, the Yellowness Index is smaller than 1 across the entire width of the fibrous web. As has been demonstrated in research, this correlates with a liner basis weight that provides sufficient coverage for the intermediate ply.

Figure 4:
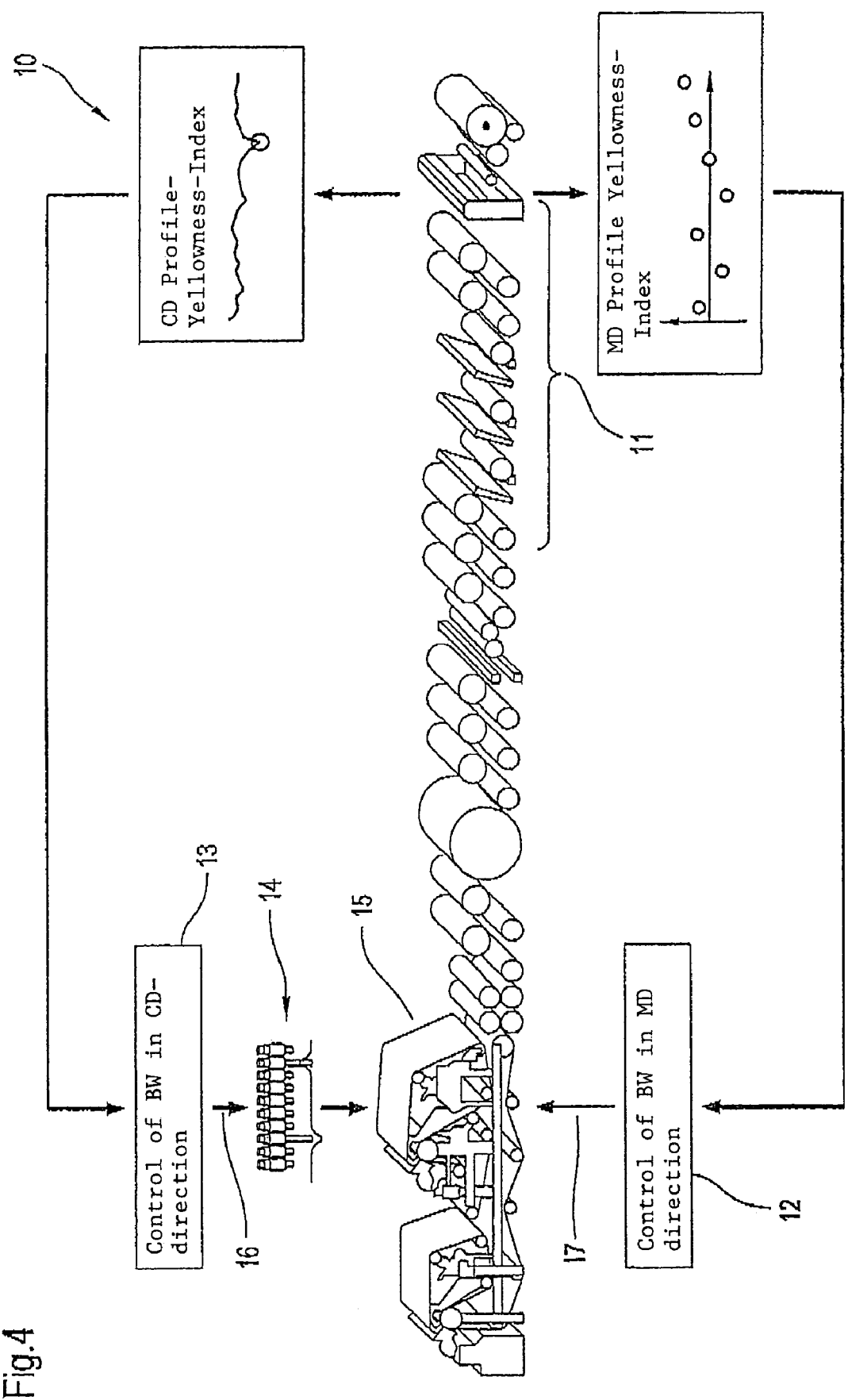
FIG. 4 illustrates a paper machine with a control sequence of an embodiment of the present invention for regulating the basis weight of a ply of the fibrous web.

Now, additionally referring to FIG. 4, there is shown a simplified perspective depiction of a paper machine 10 for the production of cardboard, there is also illustrated a control sequence for regulating the basis weight. At the end of the dryer section, the basis weight is determined in CD and in MD direction and the results transmitted to control units 12 and 13, which trigger corresponding actuators 14 in the area of the headbox in former section 15 of the liner by way of control signals 16 and 17. Actuators 14 adjust the diluting water, and adjust the slice bars and/or lips.

While this invention has been described as having a preferred design, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

What is claimed is:

1. A method for determining the basis weight of a first ply of a fibrous web which covers a second ply of the fibrous web, comprising the steps of:
    positioning an electromagnetic transmitter and an electromagnetic receiver proximate to a side of the first ply;
    radiating the fibrous web by way of said electromagnetic transmitter with at least one measuring wavelength and at least one reference wavelength, the second ply having different optical characteristics at said measuring wavelength than at said reference wavelength, said radiating step including radiating the fibrous web in at least one of a measuring wavelength range and a reference wavelength range, said measuring wavelength range being between 570 nm and 690 nm;
    receiving, by said receiver, a measuring signal which is returned at said measuring wavelength and a reference signal that is returned at said reference wavelength; and
    determining the basis weight of the first ply by utilizing a comparison of said measuring signal and said reference signal.

2. The method of claim 1, wherein the second ply has one of a higher reflection capacity and a higher absorption capacity with said measuring wavelength than with said reference wavelength.

3. The method of claim 1, wherein said measuring wavelength range is in an IR spectral region.

4. The method of claim 1, wherein said reference wavelength range is in a blue spectral region.

5. The method of claim 1, wherein said determining step include a step of determining the basis weight (BW) by using the formula BW=A*exp(-YI*B), whereby A and B represent equipment-specific constants and YI is a value that is determined by comparing said reference signal and said measuring signal.

6. The method of claim 5, wherein said value YI is determined by a ratio between said reference signal and said measuring signal.

7. The method of claim 1, wherein said determining step includes determining the basis weight by utilizing status information and machinery parameters.

8. A method for determining the basis weight of a first ply of a fibrous web which covers a second ply of the fibrous web, comprising the steps of:
positioning an electromagnetic transmitter and an electromagnetic receiver proximate to a side of the first ply;
radiating the fibrous web by way of said electromagnetic transmitter with at least one measuring wavelength and at least one reference wavelength, the second ply having different optical characteristics at said measuring wavelength than at said reference wavelength;
receiving, by said receiver, a measuring signal which is returned at said measuring wavelength and a reference signal that is returned at said reference wavelength; and
determining the basis weight of the first ply by utilizing a comparison of said measuring signal and said reference signal, said at least one measuring wavelength includes a first measuring wavelength of approximately 280 nm and a second measuring wavelength of approximately 310 nm.

9. A method for determining the basis weight of a first ply of a fibrous web which covers a second ply of the fibrous web, comprising the steps of:
positioning an electromagnetic transmitter and an electromagnetic receiver proximate to a side of the first ply;
radiating the fibrous web by way of said electromagnetic transmitter with at least one measuring wavelength and at least one reference wavelength, the second ply having different optical characteristics at said measuring wavelength than at said reference wavelength;
receiving, by said receiver, a measuring signal which is returned at said measuring wavelength and a reference signal that is returned at said reference wavelength; and
determining the basis weight of the first ply by utilizing a comparison of said measuring signal and said reference signal, said determining step including a step of determining the basis weight (BW) by using the formula BW=A*exp(-YI*B), whereby A and B represent equipment-specific constants and YI is a value that is determined by comparing said reference signal and said measuring signal, said YI value is determined from standard color values Y and Z by using a formula YI≈(Y−Z)/Y, known as a Yellowness Index according to ASTM E-313 Standard.

10. A method for determining the basis weight of a first ply of a fibrous web which covers a second ply of the fibrous web, comprising the steps of:
positioning an electromagnetic transmitter and an electromagnetic receiver proximate to a side of the first ply;
radiating the fibrous web by way of said electromagnetic transmitter with at least one measuring wavelength and at least one reference wavelength, the second ply having different optical characteristics at said measuring wavelength than at said reference wavelength;
receiving, by said receiver, a measuring signal which is returned at said measuring wavelength and a reference signal that is returned at said reference wavelength; and
determining the basis weight of the first ply by utilizing a comparison of said measuring signal and said reference signal, said determining step including a step of determining the basis weight (BW) by using the formula BW=A*exp(-YI*B), whereby A and B represent equipment-specific constants and YI is a value that is determined by comparing said reference signal and said measuring signal, said YI value is determined from standard color values X,Y and Z by using a formula YI≈(Cx*X−Cy*Z)/Y, whereby Cx and Cy represent equipment specific constants.

11. A method for regulating a basis weight of a ply in a fibrous web, whereby the basis weight is determined at several locations in at least one of a machine direction and a cross direction, comprising the steps of:
positioning an electromagnetic transmitter and an electromagnetic receiver proximate to a side of the ply;
radiating the fibrous web by way of said electromagnetic transmitter with at least one measuring wavelength and at least one reference wavelength, the ply having different optical characteristics at said measuring wavelength than at said reference wavelength;
receiving a measuring signal by said receiver which is returned at said measuring wavelength and a reference signal that is returned at said reference wavelength;
determining the basis weight of the ply by utilizing a comparison of said measuring signal and said reference signal; and
issuing control signals from a control unit to at least one actuator, said at least one actuator controls at least one of dilution water in a headbox and an adjustment of at least one of slices and lips of said headbox.

* * * * *